United States Patent [19]

De Buck

[11] Patent Number: 5,242,303
[45] Date of Patent: Sep. 7, 1993

[54] METHOD FOR THE REALIZATION OF AN IMPLANT PROSTHESIS AND PARTS HEREBY APPLIED

[75] Inventor: Vincent De Buck, St.-Niklaas, Belgium

[73] Assignee: CEKA, naamloze vennootschap, Antwerp, Belgium

[21] Appl. No.: 734,284

[22] Filed: Jul. 9, 1991

[30] Foreign Application Priority Data

Jul. 10, 1990 [BE] Belgium .................... 09000702

[51] Int. Cl.⁵ .............................................. A61C 8/00
[52] U.S. Cl. .................................................. 433/173
[58] Field of Search ............... 433/169, 167, 172, 173, 433/174, 175, 176, 196, 201.1

[56] References Cited

U.S. PATENT DOCUMENTS

| | | | |
|---|---|---|---|
| 4,552,532 | 11/1985 | Mozsary | 433/174 |
| 4,746,293 | 5/1988 | Lundgren et al. | 433/173 |
| 4,767,328 | 8/1988 | Branemark | 433/173 |
| 4,906,191 | 3/1990 | Soderberg | 433/173 |
| 4,986,753 | 1/1991 | Sellers | 433/173 |

FOREIGN PATENT DOCUMENTS 0161295 3/1991 European Pat. Off. .
3525298 1/1987 Fed. Rep. of Germany .

OTHER PUBLICATIONS

Gerhard Geiger, "Geschiebe-Technik," Munich 1982, pp. 167–171.
"Das Kleben von Geschieben Eine neue Technik Verbiuff die Kollegen," Von Ztm. Klaus-Dieter Vollerthum aus München, Heft Mar. 1982, pp. 301–302.
"Direct Assembly Framework for Osseointergrated Implant Prosthesis," Grady C. Sellers, D.D.S., The Journal of Prosthetic Dentistry, Dec. 1989, vol. 62, No. 6, pp. 662–668.

Primary Examiner—Cary E. O'Connor
Attorney, Agent, or Firm—Foley & Lardner

[57] ABSTRACT

A method for the realization of an implant prosthesis, whereby a dental bridge structure is installed on the dental implants. Accurately positioned positioning rings are installed on the elongation pieces of the implants. A cylinder is accurately positioned on each positioning ring. Each cylinder is individually screwed down by means of a screw in relation to the implants. The cylinders are connected together in order to form a bridge structure. The positioning rings are replaced by adhesive rings. By means of screws, the bridge structure is screwed down onto the implants, whereby the play between the adhesive rings and the cylinders takes up the inaccuracy of construction of the bridge structure.

28 Claims, 2 Drawing Sheets

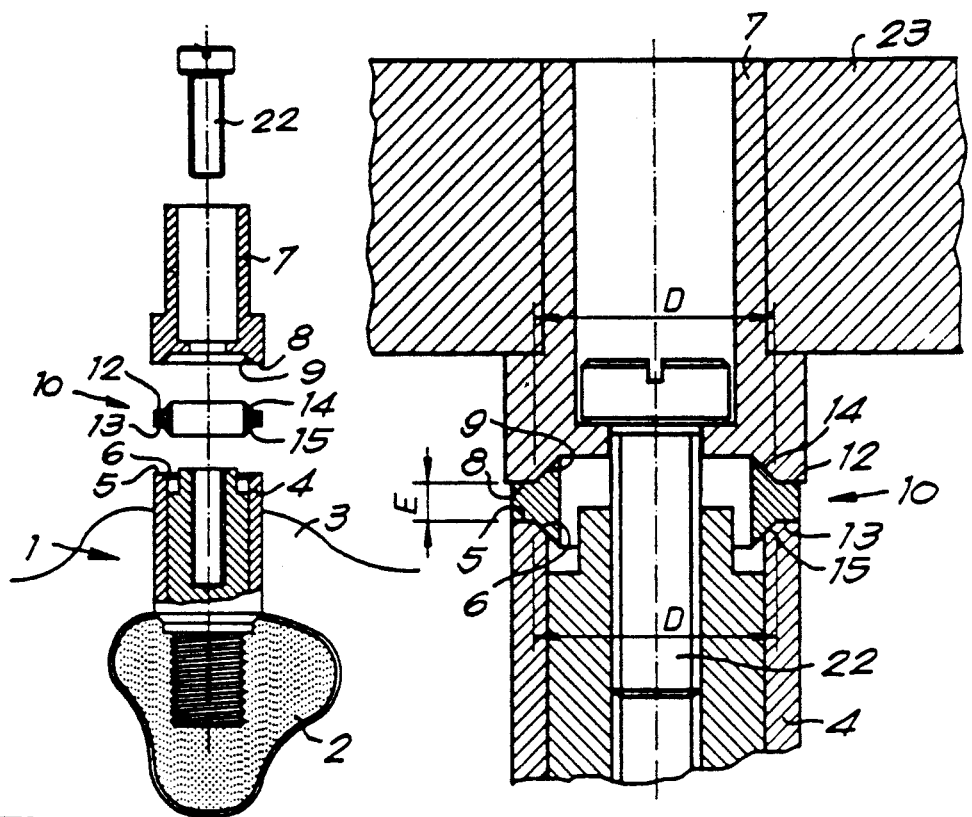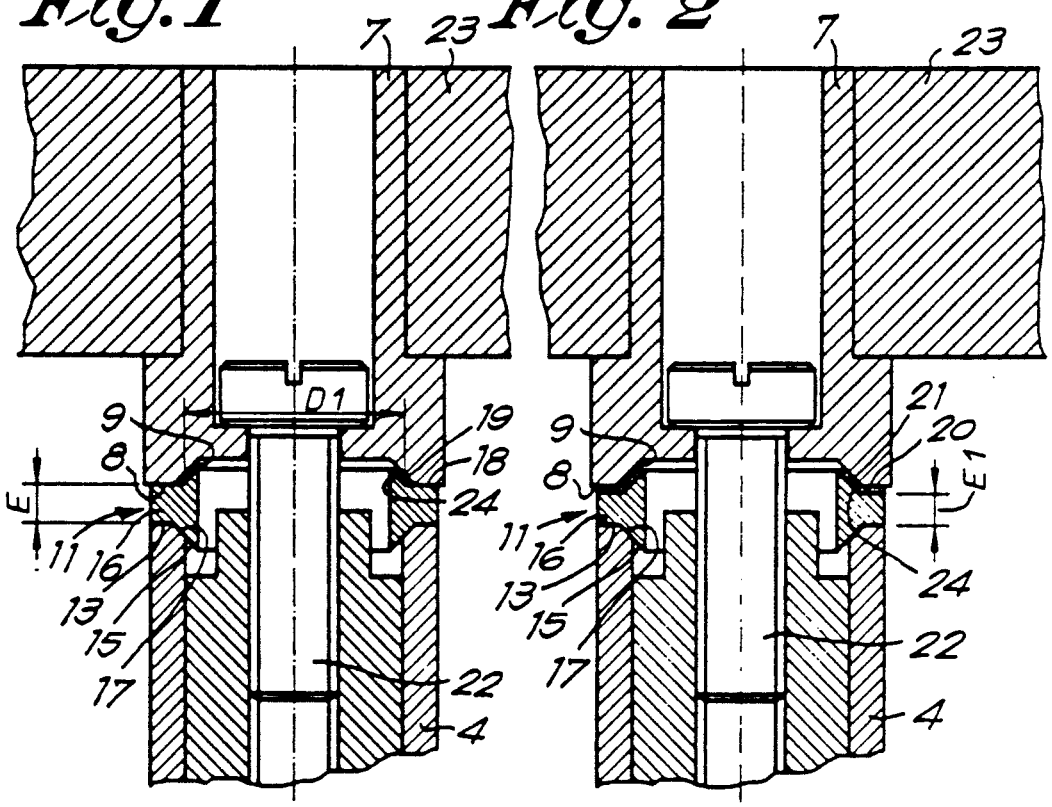

METHOD FOR THE REALIZATION OF AN IMPLANT PROSTHESIS AND PARTS HEREBY APPLIED

BACKGROUND OF THE INVENTION

1. Field of the Invention

The present invention relates to a method for the realization of an implant prosthesis as well as to parts which are applied thereby.

These parts relate more especially to a ring combination which principally consists of a positioning ring for the correct positioning in relation to each other of the parts to be connected to each other, namely, on the one hand, the dental implant and, on the other hand, the bridge structure, and a correction ring which, after the bridge structure has been realized, allows possible inaccuracies between the dental implant and the realized dental bridge structure to be adjusted and to be corrected.

2. Discussion of the Related Art

It is known that in dental prosthetics methods exist for attaching a prosthesis to a toothless jaw in a permanent manner, whereby these new methods can offer a good alternative when conventional removable prostheses do not suffice functionally or psychologically.

These known methods for attaching a prosthesis to a toothless jaw, can among others consist of the implantation, after the opening of the mucosa or mucous membrane, of a screw shaped structure of a biocompatible metal, for example of titanium, in the bone of the jaw. The the screw shaped structure is completely embedded in the bone, after which the mucosa or mucous membrane is sutured and a waiting time of up to approximately 6 months is taken into account in order to allow the bone to coalesce and osseointegrate with the implanted screw shaped structure.

After this resting period the mucosa or mucous membrane is again opened. An elongation piece is screwed onto the implant, and the mucous membrane is sutured around this elongation piece.

Such an elongation piece is provided with an internal screw thread into which an actual prosthesis can be screwed.

The level of success of such osseointegration is very high and is scientifically and clinically accepted.

Depending upon the quality of the bone, several implants can be installed. A bridge structure, for example in the form of a tooth crown or a U-shaped bar structure, can be screwed to these implants.

The metal structure is made in a plaster model by a dental technician according to the lost wax method known in industry, whereby this plaster model must represent an accurate copy of the tissues and the implants of the patient.

With the intention of obtaining an accurate copy of this mouth layout, auxiliary molding parts are screwed into the respective implants. After this an elastic molding material, such as for example, silicone, is applied, so that a negative is obtained of the tissues and of the auxiliary molding parts.

The aforementioned auxiliary molding parts are thereafter screwed out and screwed together with a so-called analog or dummy.

The auxiliary molding part side is subsequently replaced in the mold into which hard plaster is cast so that a positive copy of the mouth layout is obtained.

The analogs or dummies then sit in the location of the implants.

In this manner the work model is obtained for the dental technician.

Three often utilized techniques exist for realizing a metal bridge structure.

A first method consists in screwing down a casting cylinder onto the analogs. After this, these cylinders, are surrounded by wax and connected to each other, in order, according to the lost wax method, to surround these cylinders with metal and to connect them to each other.

A second method consists in that use is made of a synthetic material replica of the cylinders which are connected together in order to form a homogeneous metal structure according to the lost wax method.

The third method finally consists in that metal connecting elements are soldered between the cylinders.

The aforementioned cylinders can realized in any material, but use will preferably be made of cylinders in gold or in synthetic material.

The great technical problem of inaccuracy arises with all these techniques. Indeed the permitted tolerances with a similar tooth crown on ground natural elements are far greater than with implants.

Namely, with implants, no periodontal ligament exists such as is the case with natural elements.

From this it follows that inaccuracies, even in the micron range, can lead to abnormal stress zones when these are not discovered and corrected by the dentist.

Such stress zones can manifest themselves in various forms, namely through bone resorption, through the failure of osseointegration, through the loosening or breaking of screws or through the breaking of prosthetic bridge structures.

These inaccuracies can be caused, either during the molding technique, for example by not screwing the analogs tight enough, or because of the intercondylar distance increase during the molding of the lower jaw with open mouth, or even through the change of shape of the molding material or of the hard plaster, which is described as an incorrect work model, etc.

As is known, the adjustment of a U-shaped bridge structure is particularly difficult with respect to several implants, thus, in practice, it is very often necessary to grind through the bridge structure and subsequently to reattach the parts by soldering, which has the great disadvantage that through the local heating of the metal bridge structure and/or the shrinkage in the solder connection, new inaccuracies appear.

In order to avoid these inaccuracies, in other words, in order to avoid soldering or integral casting, the use has already been suggested of composite materials, such as among others described in the European patent application no. 0.161.295 and in the German patent application no. 35 25 298.

With the same intention, it has already been suggested to connect the prosthetic parts to each other by gluing, such as for example described in:

Gerhard Geiger, "Geschiebe-Technik", Munich 1982, pgs 167 to 171;

"Das Dental Labor", Heft 3/82, pgs. 301 to 302.

In the article "Direct assembly framework for osseointegrated implant prothesis" by Grady C. Sellers, D.D.S. from "The journal of prosthetic Dentistry", Dec. 1989, volume 62, number 6, pgs. 662–668, a method is further described whereby parts for an implant prosthesis are intraorally connected to each other by means of composite, to avoid stress through inaccuracies, on the one hand, and to avoid additional correction techniques, on the other hand.

With this known technique a metal support ring is installed on the implant, after which a metal structure is realized over these support rings.

The support rings and the metal structure are subsequently intraorally connected to each other by means of a composite glue.

This technique has among others a disadvantage that the metal structure, which is mounted to fit precisely around the support rings, must be ground on the inside when a distortion or inaccuracy occurs.

The size of this distortion or inaccuracy can only determined after the grinding.

When it is finally decided to grind through the bridge structure and to solder the parts to each other, the individual correct fit no longer exists.

SUMMARY OF THE INVENTION

The present invention relates to a method for the realization of dental bridge structures as well as to the parts which are thereby applied and with which the disadvantages of the known techniques are totally excluded.

The present invention more especially relates to a ring combination which can be applied with a suitable attachment structure which shows a preplanned spacious notch opposite each implant in order to obtain maximum play for taking up inaccuracies, whereby the possibility is offered of effecting a precise starting situation for a possible soldering procedure.

The ring combination for this purpose principally consists of two different rings, namely a positioning ring, on the one hand, and an adhesive ring, on the other hand.

The positioning ring hereby shows an inside, bottom, fitting perfectly onto the implant in question, and an outside, top, fitting perfectly onto the attachment structure.

The attachment structure is principally formed by cylinders in gold or in synthetic material which are placed on the positioning rings in question. These cylinders are, by means of the so-called lost wax technique, connected to each other in order to form a U-shaped bridge structure.

Subsequently, the work is continued with the aforementioned adhesive ring which shows a perfectly fitting inside bottom, but an outside and/or top which permits limited lateral and/or vertical play in relation to the bridge structure or attachment structure.

At this time, the bridge structure or attachment structure together with the adhesive rings can be fitted in the mouth in order to determine whether or not work was performed on an incorrect work model and/or the possible inaccuracy lies within the permitted limits. If this is not the case, the bridge structure is divided into two or more parts. By means of the positioning rings the bridge structure is screwed down with the dental implants in the mouth in order subsequently to connect these parts to each other with synthetic material and thereafter to solder them down together.

The advantages are thus obtained that a maximum permissible inaccuracy can be predetermined, on the one hand, and that the bridge structure or attachment structure does not have to be adjusted by grinding, so that the important contact surface remains undamaged, on the other hand.

The method for the realization of an implant prosthesis according to the invention, whereby a dental bridge structure is installed on the dental implants, principally consists in the installation of accurately positioned positioning rings on the elongation pieces of the implants; the accurate positioning of a cylinder on each positioning ring; the individual screwing down of each cylinder by means of a screw in relation to the implants in question; the connecting together of the cylinders in order to form a bridge structure; the replacement of the positioning rings by adhesive rings; and the screwing down, by means of screws, of the bridge structure onto the implants, whereby the play between the adhesive rings and the cylinders takes up the construction inaccuracy of the bridge structure.

The play between the adhesive rings and the cylinders will preferably hereby be filled up with a filling agent, for example glue, and then preferably a composite glue, through which the transfer of strength from the bridge structure to the implants occurs very uniformly. As filling agent, a product with a high compression resistance will preferably again be applied so that the aforementioned transfer of strength can occur without local distortion of the bridge structure.

The ring combination according to the invention which is applied by this method principally consists of a positioning ring which is formed by a ring with parallel surfaces and a well defined thickness whereby these surfaces are extended either internally, or externally by diverging or converging conical surfaces, on the one hand, and an adhesive ring which is formed by two parallel surfaces with a well defined thickness, whereby these surfaces are extended either internally, or externally by diverging or converging conical surfaces, whereby the inside diameter or outside diameter of the parallel surfaces of the positioning ring is equal to the corresponding inside diameter or outside diameter of the parallel surfaces of the adhesive ring.

Other ring combinations can be formed by a positioning ring and an adhesive ring whereby the conical surfaces are parallel.

BRIEF DESCRIPTION OF THE DRAWINGS

In order to show better the characteristics according to the present invention, two preferred embodiments are described hereafter with reference to the attached drawings, in which:

FIG. 1 shows in cross-section an exploded view of a dental prosthesis according to the invention;

FIG. 2 shows on larger scale the assembly of the parts according to FIG. 1;

FIG. 3 is a view similar to that of FIG. 2 but whereby the positioning ring according to the invention is replaced by a so-called adhesive ring according to the invention;

FIG. 4 is a view similar to that from FIG. 3, but for an embodiment variant;

DETAILED DESCRIPTION OF THE PREFERRED EMBODIMENTS

Figure 5:
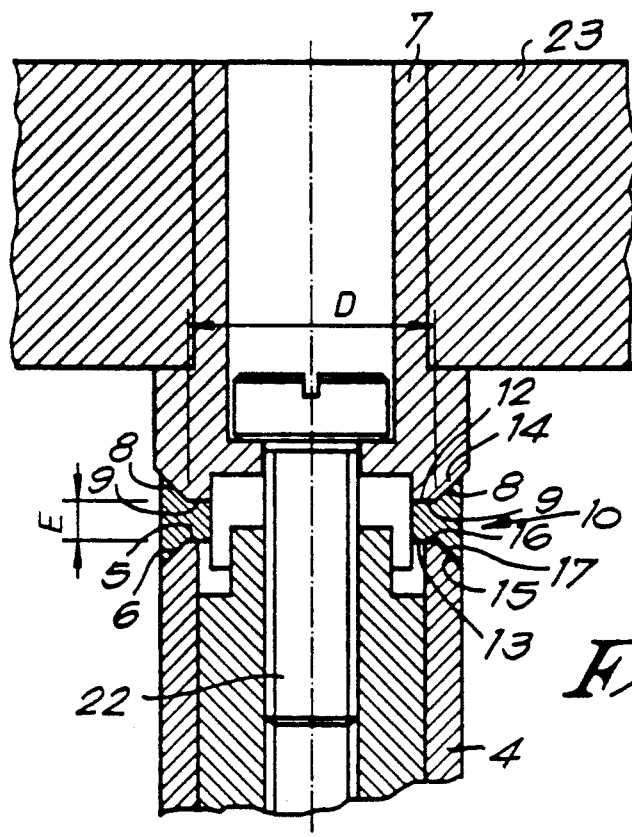
FIGS. 5 and 6 show variants of FIG. 2.

In FIG. 1, an implant 1 is shown which is attached in suitable manner in the bone 2 that is surrounded by the mucosa or mucous membrane 3 and whereby the elongation piece 4 is provided with a free upper extremity that shows a flat top edge which is internally extended by a conical wall 6.

Opposite the implant 1, a cylinder 7 in gold or synthetic material is shown, of which the free lower extremity shows a flat bottom edge 8 which is internally extended by a conical wall 9.

The inside diameter D of the flat top edge 5 is equal to the inside diameter D of the bottom edge 8, while the conical walls 6 and 9 are disposed at the same angle, of for example 45 degrees, in relation to the central axis of the implant 1, and to the cylinder 7.

According to the invention two rings are applied, namely a so-called positioning ring 10 and a so-called adhesive ring 11. The positioning ring 10 has an external thickness E which bounds two flat walls, respectively 12 and 13, of which the inside diameter is equal to D and whereby from this inside diameter D the walls 12 and 13 are extended by diverging conical walls, respectively 14 and 15, which are disposed at an angle, in relation to the central axis of the ring 10, which corresponds to the angle of the aforementioned conical walls 6 and 9, of the implant 1 and of the cylinder 7, respectively.

In the embodiment according to FIG. 3, the adhesive ring 11 also has a thickness E and is in a similar manner to the positioning ring 10 provided with a similar bottom wall 16 and a similar conical wall 17, while the top edge 18 thereof is produced wider up to a diameter D1 which is slightly larger than the aforementioned diameter D in order subsequently to he extended by a conical wall 19 which is disposed at the same angle as the angle of the conical wall 14 of the positioning ring 10.

In the embodiment according to FIG. 4, an adhesive ring 11 is applied with a bottom wall 16 and a conical wall 17, on the one hand, and a top wall 20 and a connecting conical wall 21, on the other hand, whereby the walls 16, 17, 20 and 21 respectively correspond to the walls 13, 15 and 12, 14 of the positioning ring 10, but whereby in this case the thickness E1 of the adhesive ring 11 is slightly less than the thickness E of the positioning ring 10.

The realization of an implant prosthesis according to the invention is essentially effected as follows.

A positioning ring 10 is installed on each implant 1 in order to subsequently place a cylinder 7 in gold or synthetic material on such ring, whereby it is automatically achieved that each cylinder 7 is perfectly situated in relation to the implant 1 because of the cooperation in essence of the conical walls 14, 15 of the positioning ring 10 with the conical walls 6 and 9 of the implant 1 and the cylinder 7.

Also the distance E between the parts 1 and 7 is hereby automatically determined, whereby the connection of a cylinder 7 to an implant 1 is achieved by the screwing on of a screw 22.

Mistakes are hereby totally excluded because, for example of the fact that the positioning ring 10 is produced completely symmetrically and therefore can never be installed incorrectly.

Subsequently the cylinders 7 are connected to each other, by means of the known so-called lost wax technique, so that a U-shaped bridge structure 23 is obtained.

This bridge structure is subsequently removed by unscrewing the screws 22, after which the positioning rings 10 are replaced by adhesive rings 11, either of the type as shown in FIG. 3, or of the type as shown in FIG. 4.

In the case of adhesive rings according to figure, only a lateral inaccuracy will be able to be taken in, while in the case of adhesive rings as shown in FIG. 4 both a lateral inaccuracy and a vertical inaccuracy will be able to be taken up, without a vertical raising of the entire bridge structure developing.

The bridge structure 23 is subsequently fitted in the mouth together with the adhesive rings 11 in question in order to determine whether or not work was performed on an incorrect work model and/or whether the possible inaccuracy lies within the permitted limits.

If this is the case, the adhesive rings 11 will by means of a suitable glue 24 be attached to the cylinders 7, to the bridge structure 23 and screwed down onto the implants so that, after hardening of the glue 24, an implant prosthesis is obtained whereby every stress through inaccuracy is totally excluded.

When during the fitting of the bridge structure with the adhesive rings in the mouth it is determined that the aforementioned inaccuracies however do not fall within the permitted limits, in other words are greater than the play which is provided, between the bridge structure 23, more especially the cylinders 7 and the adhesive rings 11, the bridge structure 23 will be divided into two or more parts, for example by grinding, and subsequently again be connected to the implants 1, by screwing down, with insertion of positioning rings 10.

Hereafter these parts will by means of synthetic material be connected to each other and thereafter be soldered to each other. After this the bridge structure 23, as described above, will be provided with adhesive rings 11 which by means of, for example, glue 24 are installed in the cylinders 7. After the installation of such bridge structure 23 with adhesive rings 11 in the mouth, by screwing down the screws 22, a correct relative placement of the bridge structure 23 in relation to the implants 1, is automatically achieved so that after hardening of the glue 24 the bridge structure 23 will remain perfectly in the same place in relation to the implants 1 without any stress being caused through inaccuracy.

Figure 6:
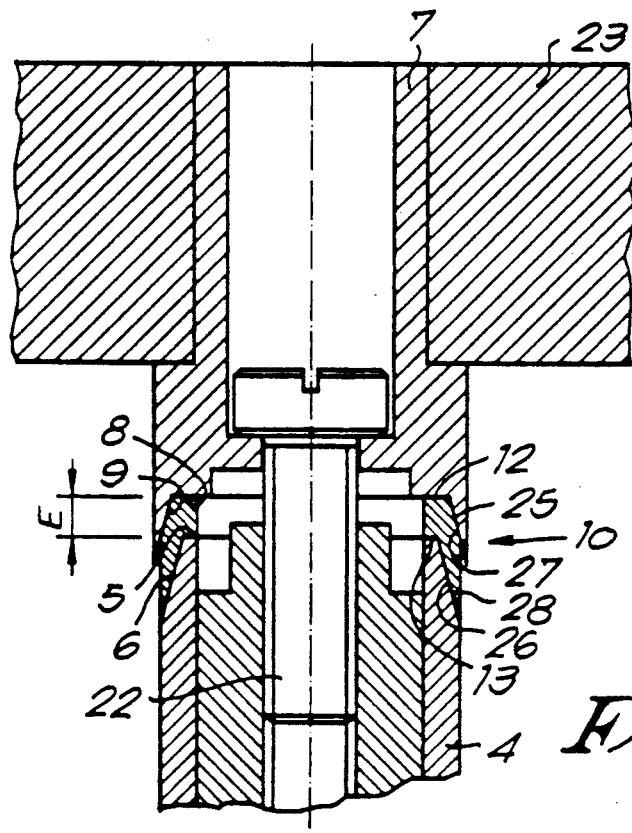

In FIGS. 5 and 6, two more variants are shown whereby, in the embodiment according to FIG. 5 the positioning ring is identical to the positioning ring according to figure 2, but provided externally with conical surfaces 14 and 15, which signifies that the conical surfaces 6 and 8 of the implants 1, respectively of the cylinders 7 are also provided on the outside in corresponding manner.

The adhesive ring 10 which is hereby utilized will also be provided with conical surfaces 15, 19, respectively 15, 21 as was the case with the adhesive rings according to FIGS. 3 and 4.

In the embodiment according to FIG. 6 a positioning ring 10 is shown which is provided with two parallel surfaces 12, 13 each of which is externally extended by parallel surfaces 25, 26 which in this case are directed downward and which correspond to conical surfaces 27, 28, respectively in the cylinders 7 and the implants 1.

Adhesive rings will obviously also be provide in this case which correspond to the positioning rings according to FIG. 6 in order to permit play between the cylinders 7 and the adhesive rings 11.

It is clear that the realization of an implant prosthesis by means of positioning rings 10 according to FIGS. 5 and 6 and the adhesive rings 11 corresponding to them is effected in the same manner as described above in relation to the embodiments according to FIGS. 2 to 4.

The present invention is in no way restricted to the embodiments described as examples and shown in the attached drawings.

I claim:

1. Method for the realization of an implant prosthesis, whereby a dental bridge structure is installed on the dental implants having elongation pieces, comprising the steps of:
   installing accurately positioned positioning rings (10) on the elongation pieces (4) of the implants (1);
   accurately positioning a cylinder (7) on each positioning ring (10);
   individually screwing down each cylinder (7) in relation to the implants by means of a screw (22);
   connecting the cylinders (7) together in order to form a bridge structure (23);
   replacing the positioning rings (10) by adhesive rings (11); and
   screwing down, by means of the screws (22), the bridge structure (23) onto the implants (1), whereby the play between the adhesive rings (11) and the cylinders (7) takes up an inaccuracy in construction of the bridge structure (23).

2. Method according to claim 1, further comprising the steps of, after the positioning rings (10) have been replaced by adhesive rings (11), fitting the bridge structure (23) in the mouth, determining if the inaccuracy remains within the play between the cylinders (7) and the adhesive rings (11), and screwing down the bridge structure (23) by means of the screws (22) onto the implants (1), after applying a filling agent between the adhesive rings (11) and the cylinders (7).

3. Method according to claim 1, further comprising the steps of, after the positioning rings (10) have been replaced by adhesive rings (11), fitting the bridge structure (23) in the mouth and, if the inaccuracy is greater than the play which is provided between the cylinders (7) and the adhesive rings (11), dividing the bridge structure into two or more parts; screwing down the divided parts to the implants by means of positioning rings (10) and screws (22); connecting the divided parts (1), to each other by means of synthetic material, soldering the divided parts, next fitting the bridge structure (23) in the mouth with insertion of adhesive rings (11), and, if the inaccuracy is within the play which is provided between the cylinders (7) and the adhesive rings (11), screwing down the bridge structure (23) onto the implants (1) by means of screws (22), after applying a filling agent (24) between the adhesive rings (11) and the cylinders (7).

4. Method according to claim 1, further comprising the step of applying a filling agent between the adhesive rings and the cylinders.

5. Method according to claim 4, wherein the filling agent (24) is a relatively quick hardening anaerobic type.

6. Method according to claim 5, wherein the filling agent (24) has a high compression resistance after hardening.

7. Method according to claim 4, wherein eh filling agent (24) is formed by a glue.

8. Method according to claim 7, wherein the glue is a composite glue.

9. An implant prosthesis for installing a dental bridge structure on dental implants having elongation pieces, produced in accordance with the process of claim 1.

10. An implant prosthesis according to claim 9, wherein the positioning ring is formed by a first ring with at least two first parallel surfaces extending to first internal conical surfaces and first external conical surfaces, and has a first well defined thickness; and the adhesive ring has two second parallel surfaces extending to second internal conical surfaces and second external conical surfaces, and has a second well defined thickness.

11. The implant prosthesis according to claim 10, wherein the first internal conical surfaces are diverging.

12. The implant prosthesis according o claim 10, wherein the first external conical surfaces are diverging.

13. The implant prosthesis according to claim 10, wherein the first external conical surfaces are parallel.

14. The implant prosthesis according to claim 10, wherein the second internal conical surfaces are diverging, the second parallel surface having an inside diameter (D1) greater than an inside diameter (D) of the first parallel surface (13).

15. The implant prosthesis according to claim 10, wherein the second internal conical surfaces are diverging, one of the second parallel surfaces having an outside diameter greater than an outside diameter of the first parallel surface (13).

16. The implant prosthesis according to claim 10, wherein the second external conical surfaces are parallel and one of the second parallel surfaces has an outside diameter less than an outside diameter of a corresponding surface (12) of the positioning ring (10).

17. The implant prosthesis according to claim 10, wherein the second internal conical surfaces are diverging and one of the second parallel surface has an inside diameter (D) equal to an inside diameter (D) of the other second parallel surface (13).

18. The implant prosthesis according to claim 10, wherein the conical surfaces (14, 15, 19, 21) have angles which are equal to each other.

19. The implant prosthesis according to claim 18, wherein the angles of the conical surfaces (14, 15, 19, 21) are at 45 degrees in relation to a central axis of the positioning ring (10) and the adhesive ring (11).

20. The implant prosthesis according to claim 10, wherein the thickness (E) of the adhesive ring (11) is equal to the thickness (E) of the positioning ring (10).

21. The implant prosthesis according to claim 10, wherein the thickness (E1) of the adhesive ring (11) is less than the thickness (E) of the positioning ring (10).

22. An implant prosthesis according to claim 10, further comprising the elongation piece of the implant, wherein the elongation piece has a free top extremity with a flat top wall; and the cylinder has a free bottom extremity formed by a flat bottom wall.

23. The implant prosthesis according to claim 22, wherein the flat top wall (5) is extended internally by a conical wall (6).

24. The implant prosthesis according to claim 22, wherein the flat top wall (5) is extended externally by a conical wall (6).

25. The implant prosthesis according to claim 22, wherein the flat bottom wall (8) is extended internally by a conical wall (9).

26. The implant prosthesis according to claim 22, wherein the flat bottom wall (8) is extended externally by a conical wall (9).

27. The implant prosthesis according to claim 22, wherein the top wall and bottom wall have an inside diameter which is equal to an inside diameter (D) of the first parallel surfaces of the positioning ring (10),.

28. The implant prosthesis according to claim 22, wherein the top wall and bottom wall have an outside diameter which is equal to the outside diameter of the first parallel surfaces of the positioning ring (10).

* * * * *